(12) United States Patent
Ruminski

(10) Patent No.: US 8,037,746 B2
(45) Date of Patent: Oct. 18, 2011

(54) ADHESIVE CREEP FIXTURE

(75) Inventor: Jason Ruminski, Delaware, OH (US)

(73) Assignee: Honda Motor Co., Ltd., Tokyo (JP)

( * ) Notice: Subject to any disclaimer, the term of this patent is extended or adjusted under 35 U.S.C. 154(b) by 512 days.

(21) Appl. No.: 12/331,001

(22) Filed: Dec. 9, 2008

(65) Prior Publication Data

US 2010/0139385 A1    Jun. 10, 2010

(51) Int. Cl.
*G01N 17/00* (2006.01)
*G01B 21/08* (2006.01)

(52) U.S. Cl. ..................................... 73/150 R
(58) Field of Classification Search ............ 73/150
See application file for complete search history.

(56) References Cited

U.S. PATENT DOCUMENTS

| | | | |
|---|---|---|---|
| 2,826,065 A | 3/1958 | Grimes | |
| 3,090,225 A | 5/1963 | Hollar et al. | |
| 3,214,971 A | 11/1965 | Hammond, Jr. | |
| 3,741,005 A | 6/1973 | Dauth et al. | |
| 5,649,447 A | 7/1997 | Van Avery | |
| 5,853,895 A | 12/1998 | Lewno | |
| 5,911,166 A | 6/1999 | Cowan | |
| 6,068,719 A | 5/2000 | Lewno | |
| 6,319,344 B1 | 11/2001 | Lewno | |
| 6,846,039 B2 | 1/2005 | Lewno | |
| 2004/0214947 A1 | 10/2004 | Lewno | |
| 2011/0111220 A1* | 5/2011 | Takarada et al. | 428/345 |

FOREIGN PATENT DOCUMENTS

| | | | |
|---|---|---|---|
| DE | 43 07 053 | | 9/1994 |
| DE | 4307053 A1 * | | 9/1994 |
| GB | 2 368 644 | | 5/2002 |
| JP | 09-061340 | | 3/1997 |
| JP | 2006-300549 | | 11/2006 |
| JP | 2006300549 A * | | 11/2006 |

* cited by examiner

*Primary Examiner* — Lisa Caputo
*Assistant Examiner* — Jamel Williams
(74) *Attorney, Agent, or Firm* — Plumsea Law Group, LLC; Mark E. Duell

(57) ABSTRACT

The invention provides a test apparatus capable of testing an adhesive bond in multiple loading modes, such as in tension and in shear. The test apparatus includes a test frame, a force generator, and a force transfer arm. The test frame is configured so that the force generator may be attached to the test frame in a plurality of locations, where each location allows for a different loading mode to be tested. The test apparatus also may be used within an environmental chamber for testing the adhesive bond at extreme environmental conditions.

20 Claims, 16 Drawing Sheets

ADHESIVE CREEP FIXTURE

BACKGROUND OF THE INVENTION

1. Field of the Invention

This invention relates to adhesive creep fixtures, and more particularly to an adhesive creep fixture configured to test adhesion properties in a plurality of loading modes for elements bonded to glass.

2. Description of Related Art

Adhesives are compounds that adhere or join two items together. Adhesives are extremely useful for many applications where penetrative fixation, such as screws or nails, is not feasible or desirable. Adhesives have become increasingly important in both the construction and automotive industries. One particular application where adhesives are used is adhering brackets to glass. This type of application commonly occurs with motor vehicle windows, where the glass window requires a linkage to the mechanism that lowers and raises the window.

In many instances when adhesive bonds are used to create fixation between two elements, characterizing the strength and durability of the bond created by the adhesive is desirable. This characterization becomes increasingly important for understanding the strength and durability of various compounds prior to utilizing a compound for a commercial application. Adhesive materials typically provide strength in tensile loading and shear loading. Tensile loading are types of loads that tend to pull the two bonded items apart. Shear loading are types of loads that tend to cause the two bonded items to slide relative to each other. Companies typically have test protocols in place to characterize adhesion strength of compounds in at least these two types of loading conditions.

Several solutions for testing the adhesive strength of materials have been proposed. U.S. Pat. No. 3,214,971 to Hammond et al., teaches a tester designed to measure the amount of tack an adhesive possesses. In Hammond, a patch of a tacky material, such as an adhesive, is positioned on a well within a carrier top. A probe attached to a variable speed motor is positioned in contact with the patch. The probe is attached to the motor via a carrier. A strain gauge is operatively attached to the carrier via a system of springs. When the motor is in operation, the carrier is drawn away from the patch until separation of the probe from the patch is achieved. The springs transfer the force required to separate the patch from the probe to the strain gauge.

In contrast, Japanese Patent Number JP 09-061340 to Yamagiwa teaches a method for testing a resin in shear. In Yamagiwa, a resin injection space defined by a U-shaped spacer is provided between the two items to be joined by the resin. The resin is subsequently injected into the resin injection space and hardened. A tensile tester clamps onto the materials and pulls the materials apart until fracture is achieved.

Adhesives also should be able to retain adhesion strength under various environmental conditions, such as exposure to moisture, extreme heat, or extreme cold. Adhesion testing under such harsh environmental conditions would allow the tester to understand how well the adhesive should perform when used in the real world. As such, having test fixtures capable of generating the tension and shear loads while being exposed to various environmental conditions is desirable.

Environmental chambers are laboratory test apparatus capable of tightly controlling and monitoring environmental conditions such as moisture and temperature. Environmental chambers are commonly utilized in industries where products are exposed to the elements. Environmental chambers are typically small, so the chambers generally do not have extensive space for the test articles. Therefore test equipment should be sized to fit and function within environmental chambers. Many conventional systems utilize large motorized devices that can cost tens to hundreds of thousands of dollars and are not typically capable of being exposed to environmental conditions.

Therefore, a need exists in the art for an inexpensive and reusable test apparatus capable of testing adhesive properties in multiple modes that may also be configured to perform while exposed to environmental conditions. The test apparatus should be able to be quickly switched from one test mode to another test mode. The test apparatus should be able to test actual components intended for use in commercial products. Further, the connection mechanisms between the test apparatus and the test parts should be able to isolate unintended forces from being transferred to the test parts.

SUMMARY OF THE INVENTION

An adhesive creep fixture capable of testing in multiple modes an adhesive bonding an element to glass is disclosed. A ball joint attaches the force generator of the testing fixture to the test surfaces. The ball joint allows the force generator to be readily rotated to different modes. The ball joint also isolates the test surfaces from rotational forces. Further, the ball joint allows the testing fixture to be attached to a component designed for use in a commercial product and not to a testing surface prepared solely for the purposes of testing an adhesive.

In one embodiment, the invention provides a testing apparatus comprising a first testing surface and a second testing surface adhered to the first testing surface with a layer of an adhesive. The first wall is associated with the first testing surface, and a second wall is attached to the first wall. The second wall is positioned orthogonally to the first wall. A force generator is associated with the second testing surface, wherein the force generator can generate a constant force. A force transfer arm is associated with the force generator, wherein the force transfer arm transfers the constant force from the force generator to the second surface. The force transfer arm is also associated with the second testing surface with a ball joint so that the force generator is rotatably attached to the second testing surface. The testing apparatus tests the adhesive capability of the adhesive in a first mode when the force transfer arm extends through the first wall so that the force generator is positioned against the first wall. The testing apparatus tests the adhesive capability of the adhesive in a second mode when the force transfer arm extends through the second wall so that the force generator is positioned against the first wall. The force transfer arm is rotated on the ball joint to move from the first mode to the second mode.

In another aspect, the invention provides an adhesive tester comprising a frame, a force generator attached to the frame for generating a test force, a force transfer arm configured to transfer the test force from the force generator to an adhesive layer disposed between a glass surface and a second surface, a ball joint attaching the force transfer arm to the second surface, wherein the force generator may be attached to the frame in any one of a plurality of orientations, and wherein the ball joint isolates rotational forces from being transferred from the force transfer arm to the second surface.

In another aspect, the invention provides a method of testing an adhesive, the method comprising the steps of positioning a force generator on a test frame in a first mode configuration, removably attaching a first test surface to the force generator with a force transfer arm, wherein the first test surface is adhered to a glass surface with a first layer of an adhesive, and wherein the force transfer arm is attached to the first test surface with a ball joint, applying a first load until the first layer of the adhesive fails, rotating the force transfer arm on the ball joint to position the generator on the test frame in a second mode configuration, adhering the first test surface to the glass surface with a second layer of the adhesive, and applying a second load until the second layer of the adhesive fails.

Other systems, methods, features and advantages of the invention will be, or will become, apparent to one of ordinary skill in the art upon examination of the following figures and detailed description. It is intended that all such additional systems, methods, features and advantages be included within this description and this summary, be within the scope of the invention, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

DETAILED DESCRIPTION

Figure 1:
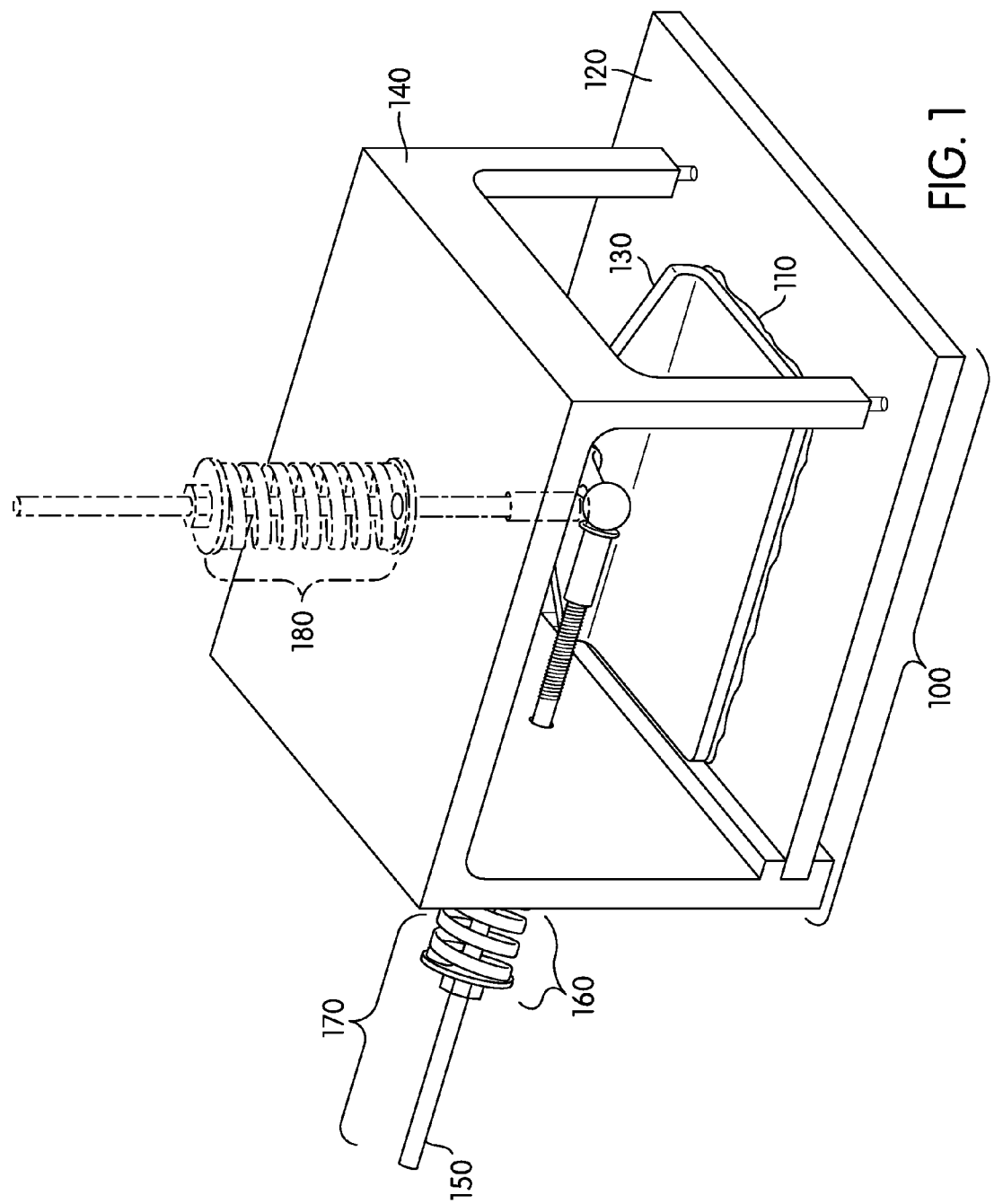
FIG. 1 is a perspective view of a testing apparatus having multiple testing modes.

An adhesion tester having multiple testing modes is disclosed. Referring to FIG. 1, an testing apparatus 100 is configured to test the strength of an adhesive layer 110 that has bonded a first surface 120 to a second surface 130. In general, adhesive layer 110 may be comprised of any commercially available adhesive or any experimental adhesive known in the art. For example, adhesive layer may comprise a glue, a two-component adhesive such as epoxy, a structural polyurethane, or the like.

First surface 120 and second surface 130 may have substantially flat surfaces as portions of larger elements. First surface 120 and second surface 130 may be made from any material capable of being bonded to another material using adhesive layer 110. First surface 120 and second surface 130 may be made from the same or different materials. In one embodiment, first surface 120 may be made from a transparent or translucent material, such as glass, polycarbonate, or other plastics, and second surface 130 may be made from a metal material, such as steel, aluminum, chrome, or the like. Such an embodiment would simulate having a metal bracket adhered to a glass window.

In one embodiment, as shown in the figures, testing apparatus 100 may be a testing jig generally including a frame 140 that includes provisions to support a force generator 160 and a force transfer arm 150. Force transfer arm 150 includes provisions to transmit the force from force generator 160 to either first surface 120 or second surface 130.

As shown in the figures, test frame 140 may be a box- or cage-like apparatus configured to be attached to either first surface 120 or second surface 130. While test frame 140 may have any shape, in the embodiment shown in FIG. 4 test frame 140 generally includes a first wall 190 positioned generally orthogonally to a cover 200. A first leg 191 and a second leg 192 extend orthogonally away from cover 200 opposite to first wall 190. This configuration provides two flat surfaces against which force generator 160 may operate, i.e., first wall 190 and cover 200. Further, this configuration allows a test operator to observe the object under test, as the areas between first wall 190 and legs 191 and 192 remain open.

In the embodiment shown in the figures, first surface 120 is larger than second surface 130. In such an embodiment, test frame 140 may be sized and dimensioned to be disposed on first surface 120 and surround or substantially surround second surface 130. In other embodiments, test frame 140 may partially surround a portion of second surface 130. Test frame 140 may be made from a sturdy material capable of testing adhesive layer 110 to failure. Test frame 140 may be made from a metal material, such as steel, stainless steel, aluminum, iron, or the like. Test frame 140 may be made from a material capable of withstanding exposure to harsh environmental conditions, such as stainless steel or a metal material coated or covered by a plastic or other protective material layer. Test frame 140 may be made using any method known in the art, such as casting, machining, or the like.

Figure 4:
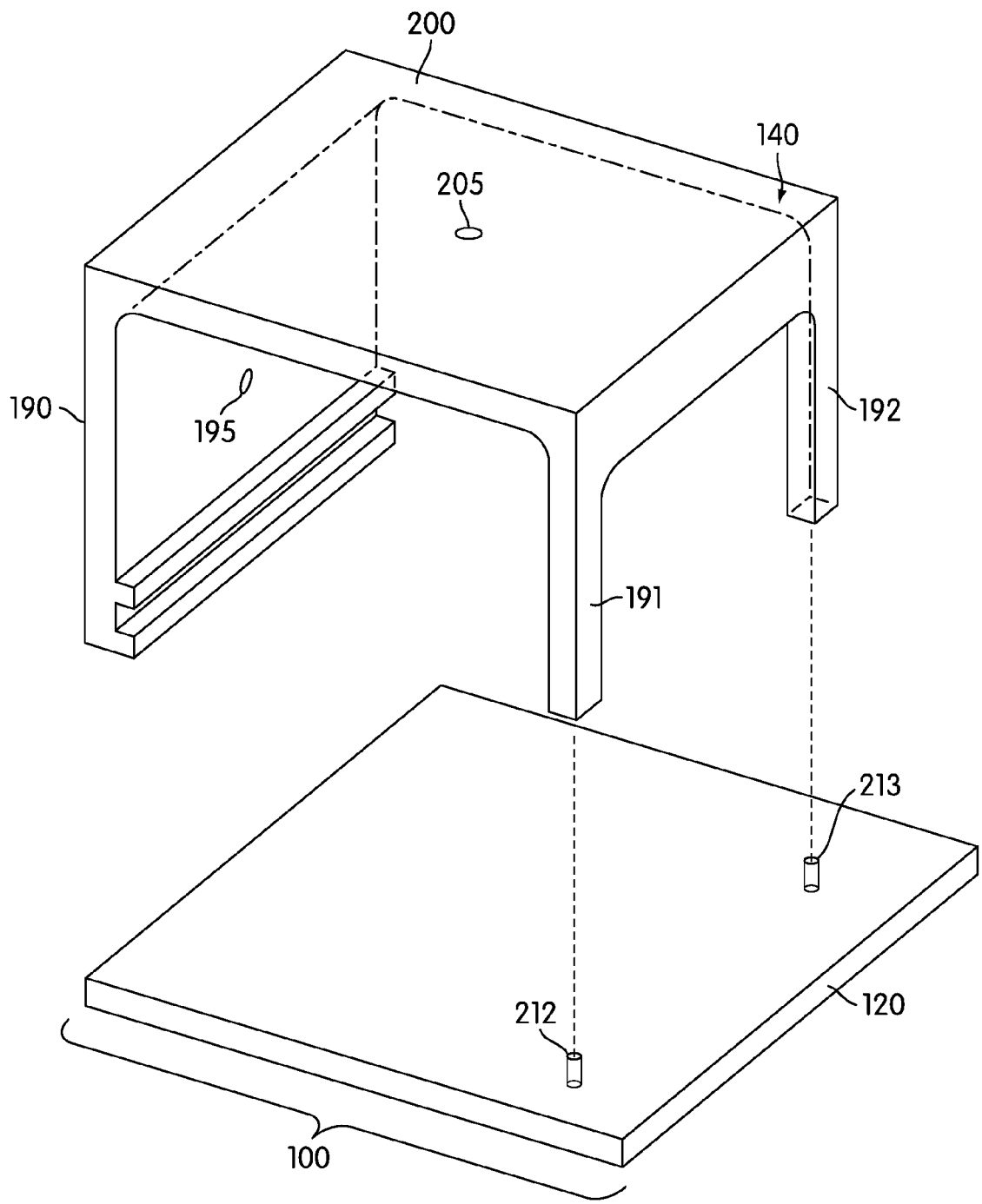
FIG. 4 is an exploded perspective view of an embodiment of a test frame for a testing apparatus having multiple testing modes.

Test frame 140 is generally configured to support force generator 160 and force transfer arm 150 so that force generator 160 may apply a force to adhesive layer 110 via force transfer arm 150. In the embodiment shown in the figures, force transfer arm 150 is configured to extend through test frame 140. As shown in FIG. 4, first wall 190 includes a first opening 195 to accommodate force transfer arm 150 when test apparatus 100 is configured for shear test mode 170. Similarly, cover 200 includes a second opening 205 to accommodate force transfer arm 150 when test apparatus 100 is configured for tensile test mode 180.

As shown in FIG. 4, first surface 120 may be configured to receive test frame 140, although in other embodiments test frame 140 may stand alone or substantially surround first surface 120. An edge of first surface 120 may be fitted into a groove or a gap disposed proximate a bottom edge of first wall 190. In other embodiments, first wall 190 may include different arrangements to receive first surface 120. For example, in some embodiments, first wall 190 may include a flange that extends underneath first surface 120. In other embodiments, first wall 190 may be similarly configured to the opposing wall and include first and second legs similar to first leg 191 and second leg 192.

First opening 212 and a second opening 213 are disposed on first surface 120 and configured to receive a fastening mechanism to fasten test frame 140 to first surface 120. Test frame 140 may be attached to first surface 120 by any known fastening mechanism known in the art. Test frame 140 may be attached to first surface 120 by a fastening system that is stronger than adhesive layer 110 and capable of withstanding harsh environmental conditions. For example, the fastening mechanism may be dowels or pegs sized and dimensioned to be inserted into openings 210, 211, 212, and 213. In another embodiments, openings 210, 211, 212, and 213 may be sized and dimensioned to receive the legs and/or walls of test frame 140.

In many conventional systems, the force generator may be the most complex and costly aspect of a test apparatus. In many conventional testing systems, these mechanisms are large motorized test systems, such as an Instron® 5500 series. In some embodiments of the invention, however, force generator 160 may be a low-cost and simplified mechanism capable of being directly exposed to harsh environmental conditions.

Figure 5:
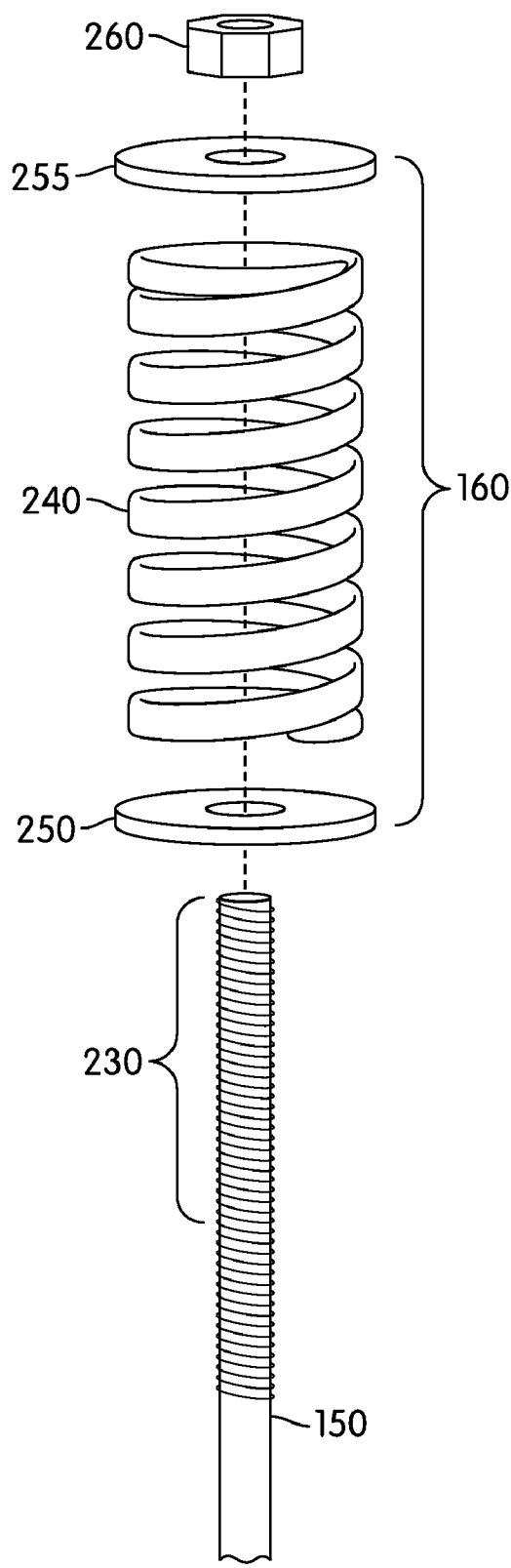
FIG. 5 is a partial exploded view of an embodiment of a force generator and a force transfer mechanism for a testing apparatus having multiple testing modes.
Figure 6:
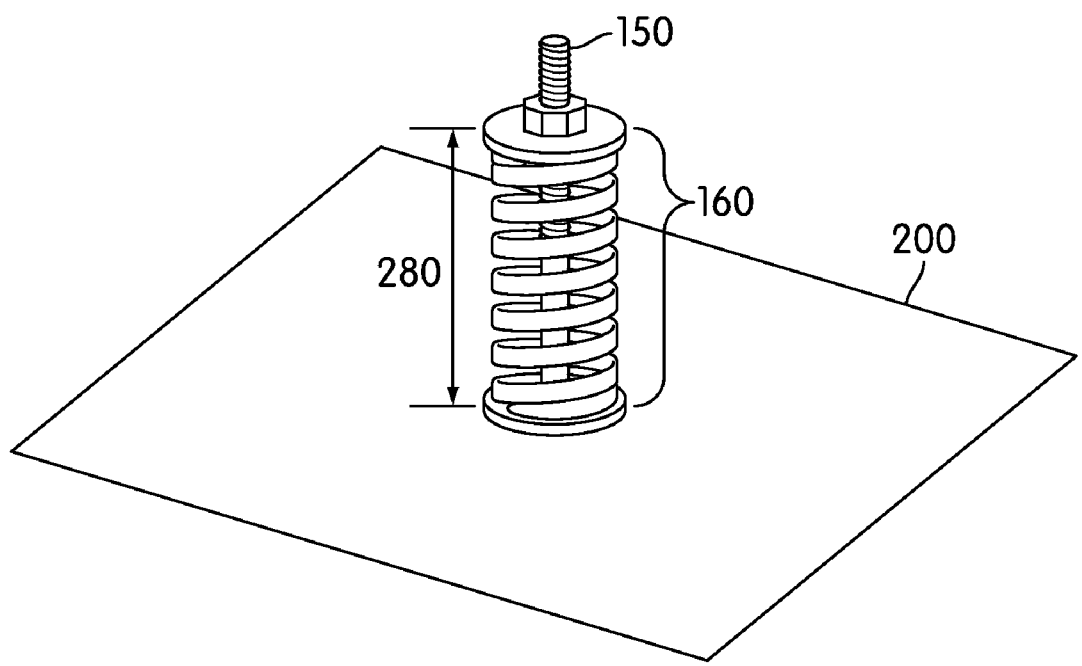
FIG. 6 is a perspective view of an assembled force generator and force transfer mechanism in an initial position.
Figure 7:
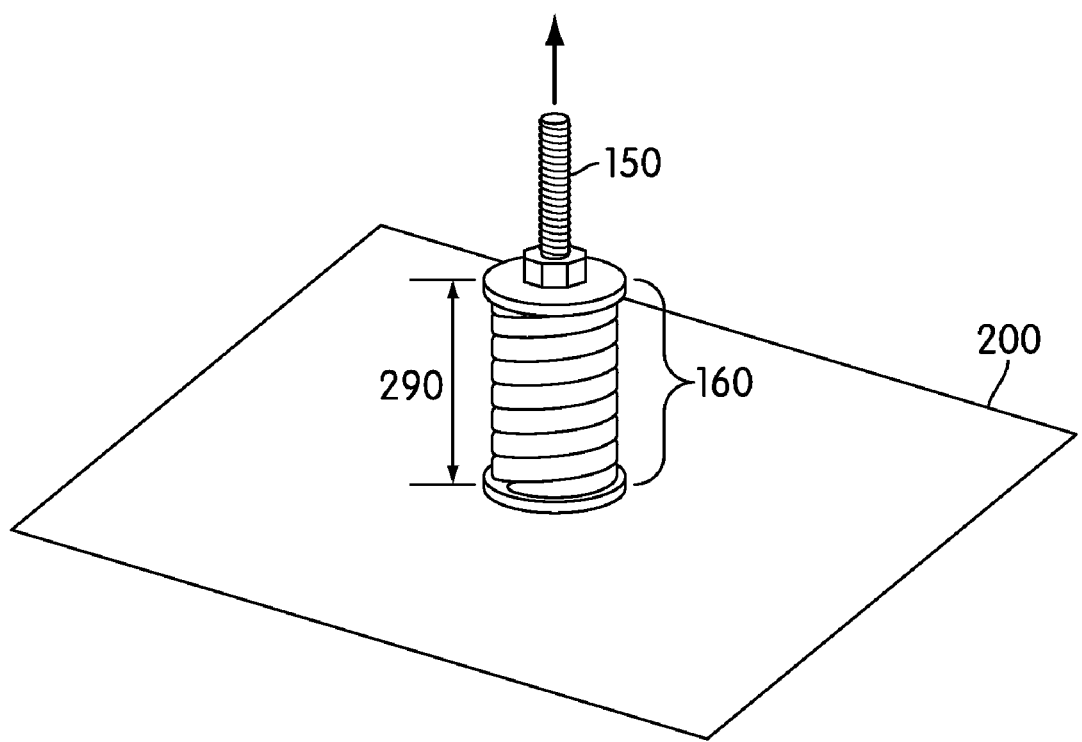
FIG. 7 is a perspective view of the assembled force generator and force transfer mechanism of FIG. 6 in a force-generating position.

FIGS. 5-7 show one embodiment of force generator 160 for test apparatus 100, where force generator 160 includes a coil compression spring 240 made of a material such as stainless steel. In other embodiments, force generator 160 may include other types of springs or made of different materials. The stiffness or spring constant of spring 240 may be selected depending upon the forces the testing protocol may require. Further, a testing protocol may suggesting using a number of different springs 240, with each spring 240 having a different spring constant. In such a test, iterations of the test may be performed, with each iteration using a new spring 240 having a greater spring constant than that of the previous iteration until adhesive layer 110 fails.

Force generator 160 may be disposed entirely outside of the box or cage formed by test frame 140. When utilizing a non-motorized force generator, force generator 160 may press against or otherwise obtain leverage from test frame 140. In the embodiment shown in the figures, as shown best in FIGS. 2 and 3, force generator 160 is generally disposed against an outside surface of one of the walls of test frame 140. Spring 240 of force generator 160 is positioned flush against test frame 140 with force transfer arm 150 extending through a center of spring 240, through test frame 140, and to second surface 130.

Force transfer arm 150 is configured to transmit the forces generated by force generator to adhesive layer 110 via mechanical linkages to both force generator 160 and second surface 130. Force transfer arm 150 may be any type of mechanical connector capable of spanning the distance and transferring loads between force generator 160 and second surface 130. In the embodiments shown in the figures, force transfer arm 150 is a threaded rod configured to be attached to the test piece, such as second surface 130. In other embodiments, force transfer arm 150 may have other configurations, such as a wire, bar, ribbon, or other structure.

As shown best in FIG. 5, force transfer arm 150 may be a bar or rod having a threaded portion 230. Force transfer arm 150 is, in this embodiment, sized and dimensioned to be inserted through spring 240 of force generator 160. Force transfer arm 150 may be made of a rigid material capable of transferring load and withstanding harsh environmental conditions. For example, force transfer arm 150 may be made from stainless steel, aluminum, chrome, or the like. In other embodiments, force transfer arm 150 may be a flexible material capable of transferring load and withstanding harsh environmental conditions. In such embodiments, force transfer arm 150 may be a cable or a ribbon made of thin portions of material, twisted or braided fibers, or the like. The material for the cable or ribbon may be metals, synthetic materials, or natural fibers. In any embodiment, force transfer arm 150 the material of force transfer arm 150 may have a high tensile strength, so that force transfer arm 150 is not likely to suffer a catastrophic failure during the testing process.

Force transfer arm 150 may be removably attachable to second surface 130. In conventional testing systems, force transfer arm 150 typically terminates in a clevis. In conventional embodiments, second surface 130 is typically a surface prepared specifically for testing, such as a surface readily attachable to a clevis. However, conventional systems lack the ability to test an actual component for use in a commercial product, such as a hinge, because standard parts are not generally configured to be attachable to a clevis. Therefore, in one embodiment, as shown in the figures and shown in detail in FIGS. 15 and 16, force transfer arm 150 is configured to be attached to second surface 130 using a ball joint attachment 152.

Figure 15:
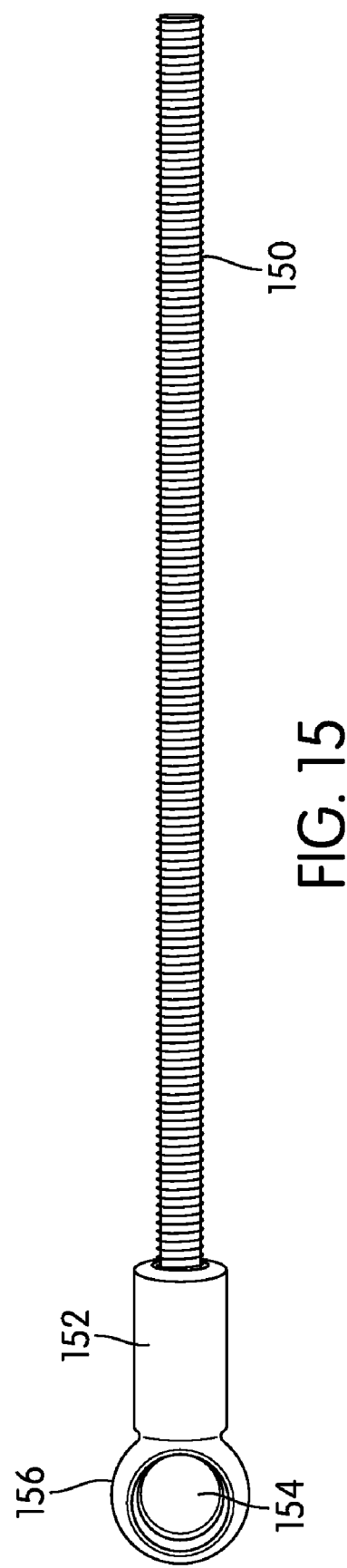
FIG. 15 is a plan view of an embodiment of a force transfer mechanism.

Ball joint attachment 152 may be attached to force transfer arm 150 using any attachment method known in the art. In some embodiments, ball joint attachment 152 may be fixedly attached to force transfer arm 150, such as with an adhesive or by welding. In other embodiments, such as the embodiment shown in the figures, ball joint attachment 152 is configured to be removably attached to force transfer arm 150. For example, as shown in FIG. 15, force transfer arm 150 is a threaded rod and ball joint attachment is configured to be threaded onto an end of force transfer arm 150.

Ball joint attachment 152 includes a head 156 having a socket 154 formed within head 156. In the embodiment shown in the figures, head 156 is a rounded portion and socket 154 is a hollowed internal portion of head 156. In other embodiments, head 156 may be completely hollow, so that socket 154 extends entirely through head 156.

Figure 16:
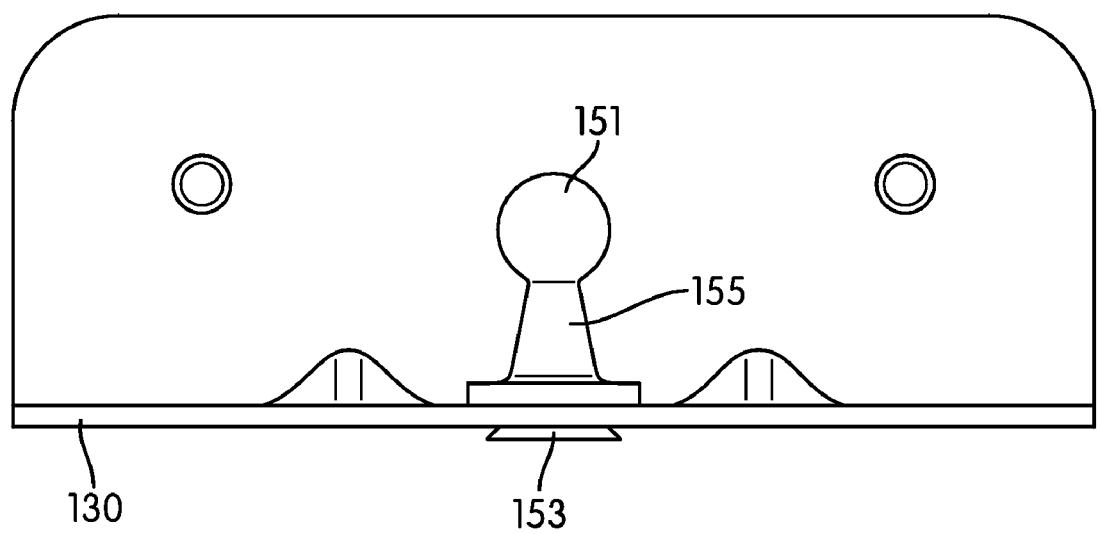
FIG. 16 is a plan view of an embodiment of a test piece.
Figure 17:
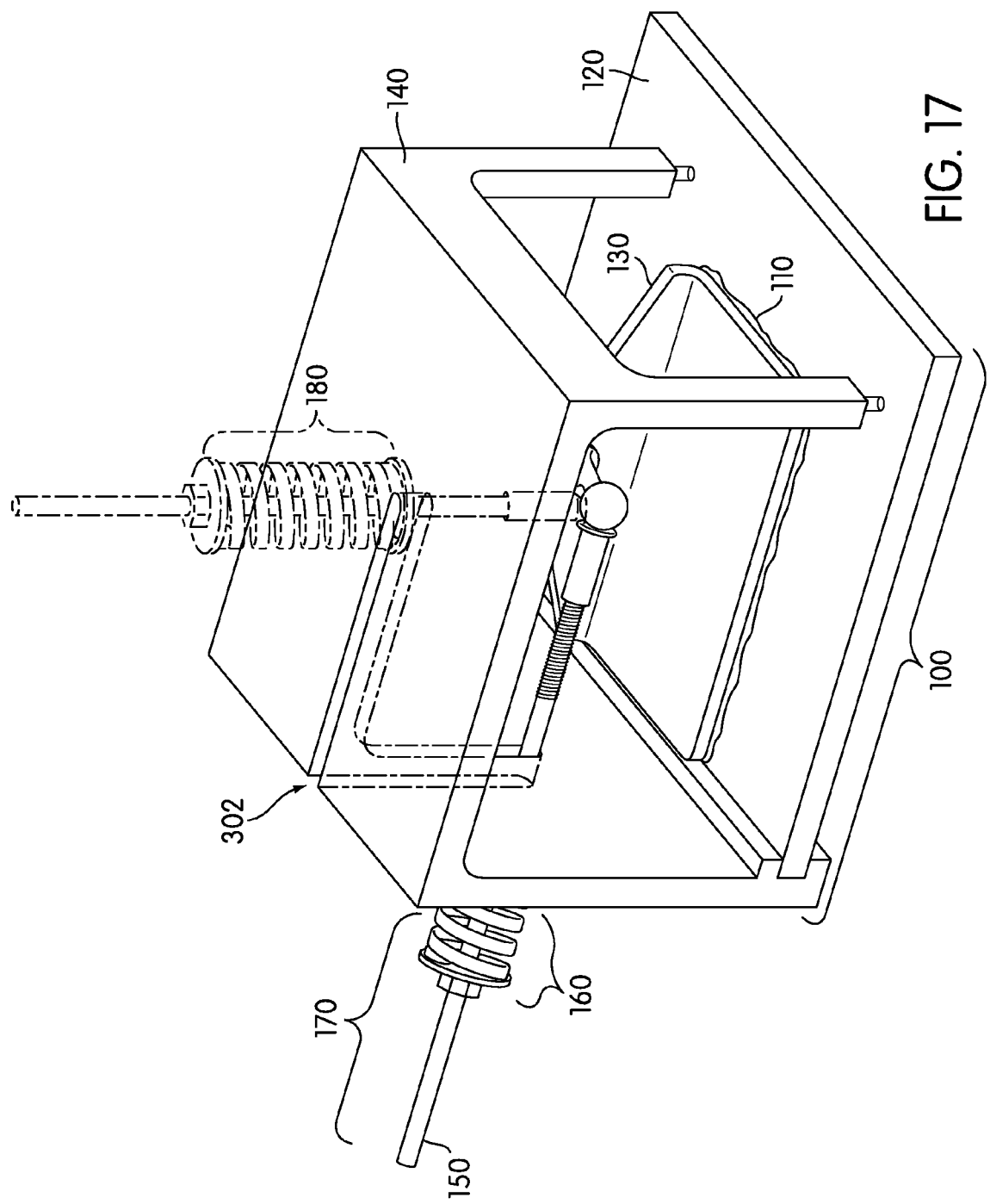
FIG. 17 is a perspective view of an embodiment of a test apparatus attached to a testing surface.
Figure 18:
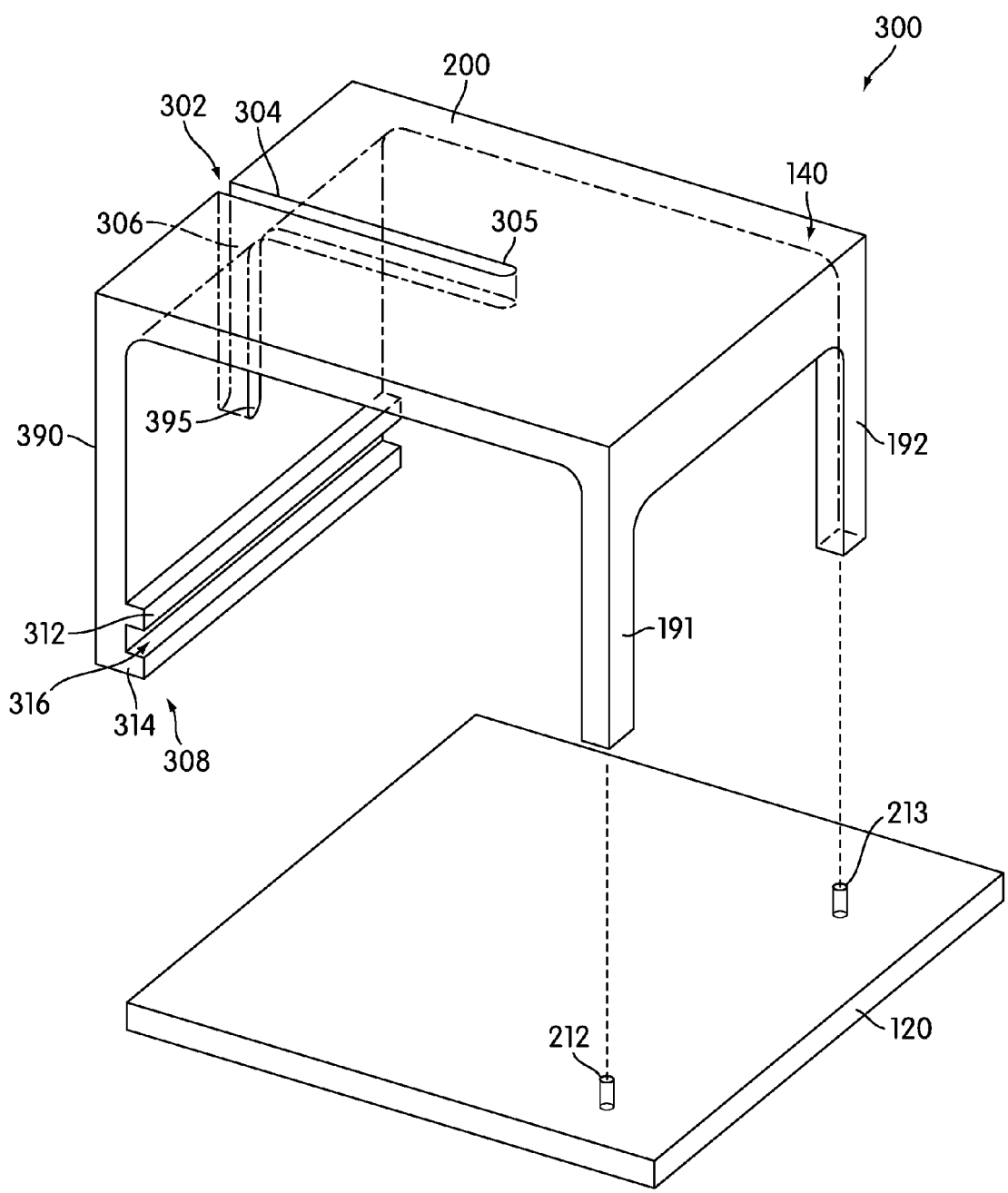
FIG. 18 is a perspective view of the testing jig removed from the testing surface.

In the embodiment shown in FIG. 16, second surface 130 includes a standard hinge. A ball element 151 is removably attached to a portion of second surface 130. Ball element 151 is sized and shaped to be received by socket 154. Ball element 151 is fixedly attached to a stem 155, which aligns with a hole or other opening provided in the standard design of second surface 130. Stem 155 is secured in position using a mechanical connector 153, which may be any type of mechanical connector known in the art, such as a pin, rivet, screw, or the like. Mechanical connector 153 passes through the opening in second surface 130 and is secured to stem 155. In other embodiments, a portion of step 155 may extend through the opening in second surface 130 so that mechanical connector 153 may be secured to stem 155. In such embodiments, mechanical connector 153 may include nuts, clips, locking washers, or similar attachment connectors. In other embodiments, mechanical connector 153 may be eliminated and stem 155 may be secured to second surface by welding, with an adhesive, or with another permanent or semi-permanent fixative.

Ball element 151 is sized and shaped to fit into socket 154 and rotate within socket 154. The outer surface of bell element 151 may contact the inner surface of socket 154 or a clearance may be provided between the two surfaces.

In some embodiments, ball element 151 may be sized and shaped to be press-fitted into socket 154 so that no additional attachments are necessary to retain ball element 151 within socket 154 for the duration of the test procedure. In other embodiments additional securing attachments may be utilized to assist in maintaining ball element 151 within socket 154. For example, in the embodiment shown in the figures, stem 155 has a frusto-conical shape, with the widest portion adjacent second surface 130 and the narrowest portion adjacent ball element 151. A removable spring clip or other collar-type device may be provided at the narrowest portion of stem 155 to prevent ball element 151 from being unintentionally removed from socket 154.

In some embodiments, such as the embodiments shown in the figures, ball element 151 may be a present a smooth, rounded surface to the inner surface of socket 154. The mating of these two surfaces allow the two surfaces to move with respect to each other. This enables force transfer arm 150 to be rotated on ball element 151 to move from one mode to another mode without detaching force transfer arm 150 from second surface 130. This feature is described in greater detail below with respect to FIGS. 17-21. In some embodiments, both the outer surface of ball element 151 and the inner surface of socket 154 may be smooth for easy rotation of ball element 151 within socket 154. In other embodiments, one or both surfaces may be provided with a texture for control of the rotation, for stepped movement of ball element 151 within socket 154, or to assist in retaining ball element 151 in a specified position within socket 154 until intentionally moved by a user.

Ball joint attachment 152 also allows any rotational forces present in force transfer arm 150 to be isolated from second surface 130. For example, if force transfer arm 150 is not perfectly orthogonally positioned with respect to the walls of frame 140, a moment arm is generated between force transfer arm 150 and the walls of frame 140. Force transfer arm 150 may then torque second surface 130 in addition to applying the shear force or the tensile force. This torque force may cause second surface 130 to delaminate or peel away from first surface instead of just inducing the perfect shear creep or perfect tensile creep. Ball joint attachment 152 will cause force transfer arm 150 to rotate slightly about the pivot of ball joint attachment 152 in response to this torque force. The torque force is thus isolated from second surface 130, which would then experience only the pure shear or pure tensile force. This may result in more accurate test results.

Force transfer arm 150 may be removably attached to force generator 160. As shown in FIG. 5, force transfer arm 150 is configured to extend through spring 240 of force generator 160. Nut 260 is configured to be threaded onto threaded portion 230 of force transfer arm 150 to maintain the positioning of force transfer arm 150 on force generator 160. Nut 260 may be sized and dimensioned to have a greater diameter than that of spring 240 so that nut 260 is not drawn through spring 240. In some embodiments, as shown in FIG. 5, an optional washer 255 may be provided between nut 260 and spring 240, where washer 255 has an outer diameter equal to or greater than that of spring 240.

In order to transfer the testing forces generated by force generator 160 to adhesive layer 110, force transfer arm 150 is connected to at least one of first surface 120 or second surface 130. In the embodiment shown in the figures, second surface 130 is smaller than and adhered to a larger first surface 120. In this embodiment, second surface 130 is configured to be connected to force transfer arm 150, while in other embodiments, force transfer arm 150 may be connected to first surface 120. The connection between force transfer arm 150 and second surface 130 may be any type of connection known in the art. In one embodiment, as shown in the figures, second surface 130 may be configured to receive an end of force transfer arm 150. For example, force transfer arm 150 may be configured with a portion that may be press-fitted into an opening on second surface 130. Other types of mechanical linkages may also be used to secure force transfer arm 150 to second surface 130, such as screws and rivets. Additionally, force transfer arm 150 may be permanently affixed to second surface 130, such as by welding, with an adhesive that is stronger than adhesive layer 110, or co-forming force transfer arm 150 and second surface 130.

To generate a force, spring 240 of force generator is compressed against one of the walls of test frame 140 by tightening a nut 260 configured to be threaded onto force transfer arm 150. This compression provides the constant force applied to second surface 130 and adhesive layer 110. FIGS. 6 and 7 show force generator 160 in position against cover 200 of test frame 140, similar to the embodiment shown in FIG. 3. As shown in FIG. 6, when force generator 160 is assembled, force transfer arm 150 extends through spring 240 and optional washers 250 and 255. Nut 260 is engaged with threaded region 230 of force transfer arm 150. Washer 250 is disposed on cover 200 with force transfer arm 150 passing through second opening 205, shown in FIG. 4. In the configuration shown in FIG. 6, force generator 160 is not applying any force. Spring 240 has an uncompressed height 280.

In FIG. 7, nut 260 has been advanced down threaded region 230 of force transfer arm 150. This action compresses spring 240 to a compressed height 290 and stores energy within spring 240. Compressed height 290 is less than uncompressed height 280. When at compressed height 290, spring 240 attempts to release the stored energy and pushes against wall 200. Because nut 260 abuts spring 240 and washer 255, spring 240 cannot return to uncompressed length 280. The force generated by spring 240 pressing against wall 200 is transferred to second surface 130 via force transfer arm 150. The force is applied in the direction depicted by the arrow in FIG. 7. Force transfer arm 150 pulls on second surface 130 and attempts to move second surface 130 away from first surface 120. The bond between second surface 130 and first surface 120 created by adhesive layer 110 resists the movement of second surface 130 with respect to first surface 120 until the strength of adhesive layer 110 is overcome by the force from force generator 160. Adhesive layer 110 may fail dramatically, such as by complete separation of first surface 120 and second surface 130. Alternatively, adhesive layer 110 may fail by "creeping", where second surface 130 moves only a small distance away from or along second surface 120.

In some embodiments, a spacer 262, as shown in FIGS. 10-14, may be used with force generator 160 so that spring 240 may be manually compressed to the same height in repeated tests so that a user may readily apply the same force to the adhesive in successive tests. Spacer 262 in some embodiments may be a hard or rigid element or grouping of elements. When upper washer 255 and nut 260 are moved along the length of threaded element 150 to abut spacer 262, upper washer 255 and nut 260 may no longer advance toward lower washer 250 because spacer 262 resists any additional motion of upper washer 255 and nut 260. In other words, the spring is limited by spacer 262 in that energy stored within the spring is capped by the distance upper washer 255 and nut 260 may travel along threaded element 150 before being stopped by spacer 262. Spacer 262 may be a sleeve configured to allow spring 240 to extend through spacer 262 or an insert that extends through spring 240. In some embodiments, spacer 262 may be configured to be positioned on only one side of spring 240.

In the embodiment shown in FIGS. 10-14, spacer 262 is a generally block-like structure that includes a first portion 261 and a second portion 263 configured to be aligned with each other and positioned around spring 240. In some embodiments, first portion 261 and second portion 263 are similarly shaped and sized. In some embodiments, first portion 261 and second portion 263 are identical in shape and size. In some embodiments, first portion 261 and second portion 263 may be dissimilarly shaped and/or sized. An upper surface 268 of spacer 262 may be generally flat and configured to abut upper washer 255. Similarly, a lower surface 269 may be generally flat and configured to abut lower washer 250. Spacer 262 may be made of a rigid material that resists deforming when subjected to forces of a magnitude anticipated to be used in testing apparatus 100. In some embodiments, spacer 262 may be made from metals, such as steel, iron, aluminum, plastics, natural or synthetic composite materials, ceramics, or any combination of these materials.

In the embodiment shown in FIGS. 10-14, first portion 261 and second portion 261 are identical in size and shape so that first portion 261 may be positioned on one side of spring 240 and second portion 263 may be positioned on the opposite side of spring 240. First portion 261 includes a first curved surface 264 and second portion 263 includes a second curved surface 265. First curved surface 264 and second curved surface 265 form a cavity 270 (shown in FIG. 11) when first portion 261 is aligned with second portion 263. Cavity 270 is configured to accommodate spring 240. In some embodiments, first curved surface 264 and second curved surface 265 have the same or similar curvatures. In other embodiments, first curved surface 264 and second curved surface 265 may have different curvatures. In the embodiment shown, first curved surface 264 and second curved surface 265 have a similar curvature to that of spring 240.

Figure 14:
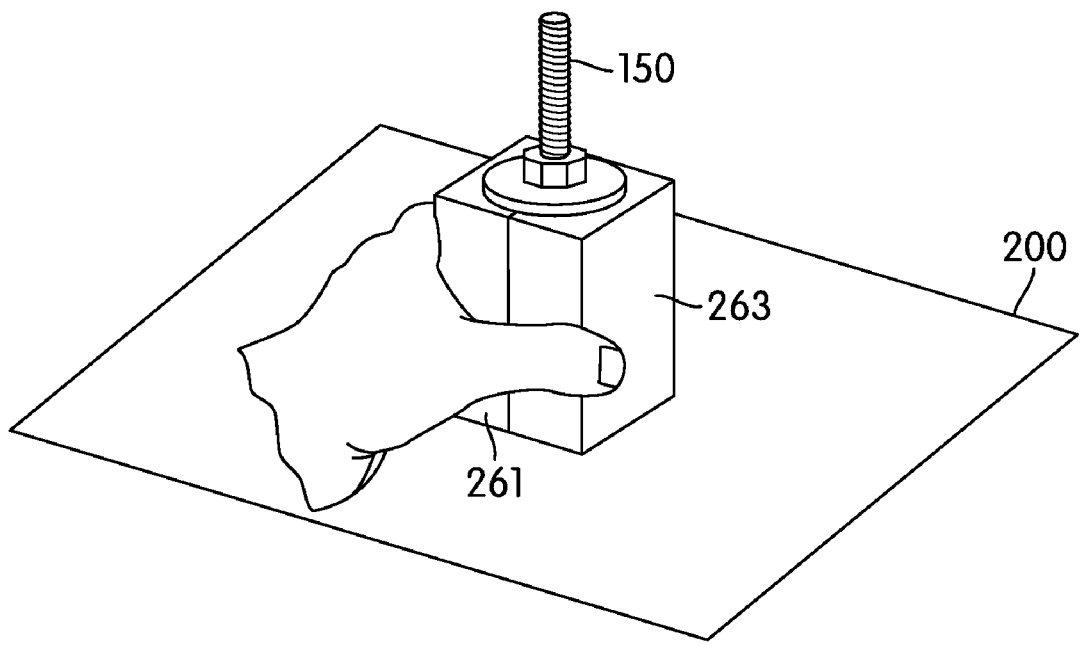
FIG. 14 is a perspective view of a portion of an embodiment of a creep tester with an embodiment of a spacer while setting the creep tester spring.

First portion 261 and second portion 263 may include one or more surfaces configured to align with each other so that first portion 261 and second portion 263 may form a unit during use. In the embodiment shown in the FIGS., first portion 261 includes a first surface 266 and second portion 263 includes a second surface 267 configured to be fitted together. In some embodiments, first portion 261 and second portion 263 may be removably attachable to each other, such as by including mechanical or magnetic linkages on or near surfaces 266 and 267. In other embodiments, first surface 266 and second surface 267 may be complementary contoured so that first surface 266 and second surface 267 engage or interlock so that the position of first portion 261 and second portion 263 do not readily shift during use. However, in the embodiment shown in the figures, first surface 266 and second surface 267 are both flat or substantially flat so that first surface 266 and second surface 267 may be pressed together, such as with a clamp or with a user's hand, as shown in FIG. 14. In such an embodiment, first surface 266 and second surface 267 are not interlocked with each other and may be readily separated. In some embodiments, first surface 266 and/or second surface 267 may include texture, such as by roughening the material or by including a coating or applying a frictional surface, so that first surface 266 and second surface 267 do not slip against each other during use.

Figure 13:
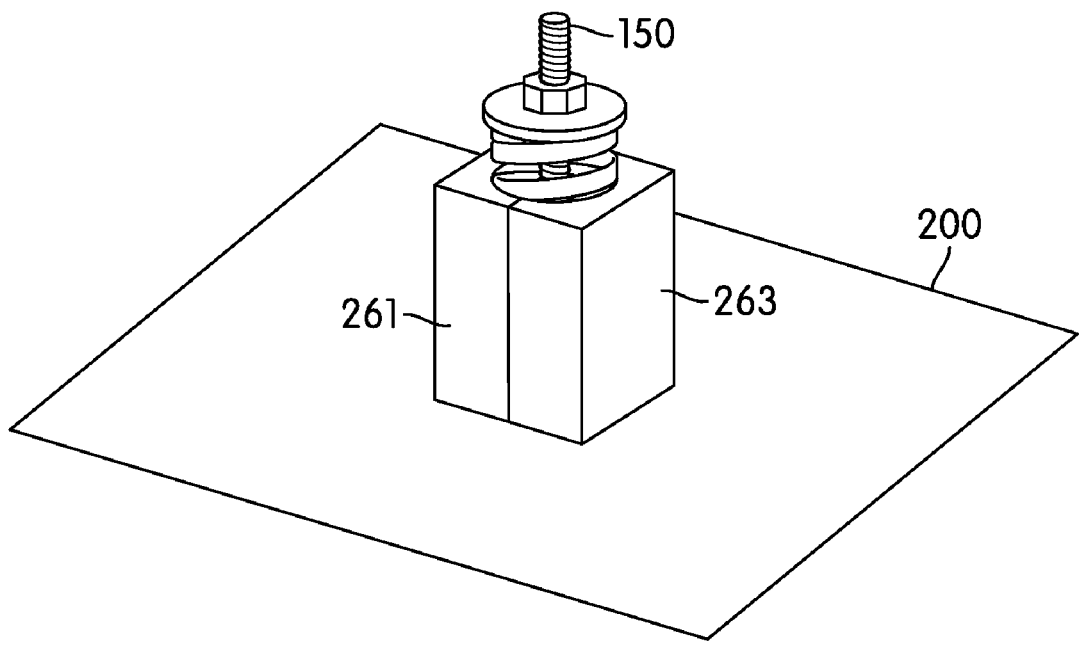
FIG. 13 is a perspective view of a portion of an embodiment of a creep tester with an embodiment of a spacer prior to setting the creep tester spring.

Spacer 262 may be used according to FIGS. 13 and 14. In an initial position, as shown in FIG. 13, spring 240 is fully extended and no energy is stored within spring 240. Spacer 262 is positioned on lower washer 250 (not shown) so that spacer 262 surrounds or substantially surrounds spring 240. Threaded element 150 and spring 240 extend through spacer 262 toward upper washer 255 and nut 260. In a loaded configuration, as shown in FIG. 14, nut 260 has been threaded onto threaded element 150 and advanced along threads 230 towards spacer 262. The two portions of spacer 262 are held together in order to maintain the relative positions of the two portions. Upper washer 255 has been advanced to rest upon or abut spacer 262. Spring 240 has been compressed so that the entirety of spring 240 is contained within spacer 262. Spring 240 now stores energy for the test. Because any one spacer will have the same height from test to test, the amount of stored energy within spring 240 will be substantially the same from test to test as long as upper washer 255 is advanced to spacer 262 for each test. Different spacers having different heights may be used as well, in order to vary the amount of stored energy within spring 240 for different tests.

The particular wall of test frame 140 against which force generator 160 is disposed may change the mode of loading for the test, providing test apparatus 100 the ability to test adhesive layer 110 in various modes. Each testing mode exposes adhesive layer 110 to a different type of force. For example, in the embodiment shown in the figures, testing apparatus 100 is able to test adhesive layer 110 in two modes: via the application of a tensile force load or the application of a shear force load. Tensile force is typically defined as the force pulling two ends of an object away from each other. In the case of adhesives, tensile force is applied in a direction perpendicular to the surfaces adhered together, thereby acting to pull the two surfaces apart. The adhesive, if possessing strength greater than the force being applied, should prevent the two surfaces from separating. Shear force is typically defined as a force applied parallel to a surface of a material. In the case of adhesives, the shear force is applied in a direction parallel to the surfaces that are adhered together. The adhesive, if possessing strength greater than the force being applied, should prevent the two surfaces from sliding or slipping against each other. Other embodiments of testing apparatus 100 may be configured to test in more than these two modes. However, for the sake of clarity, only a shear mode 170 and tensile mode 180 of testing are discussed further.

Figure 2:
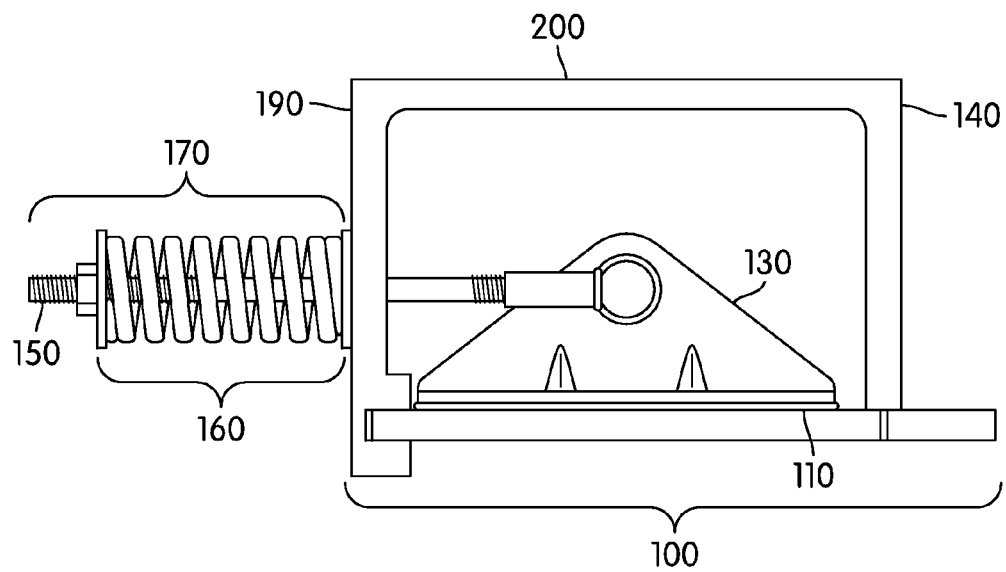
FIG. 2 shows the testing apparatus of FIG. 1 in a first testing mode.
Figure 3:
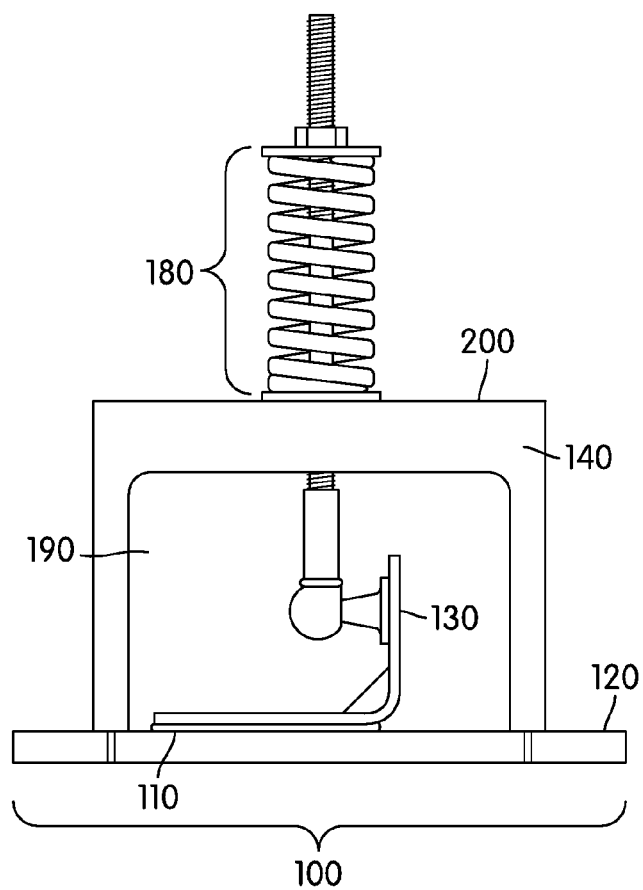
FIG. 3 shows the testing apparatus of FIG. 1 is a second testing mode.

Test frame 140 includes provisions to allow a technician or other user to readily remove force generator 160 from an initial position in a first mode and re-attach force generator 160 to test frame 140 in a second position for a second mode. For example, FIG. 2 shows testing apparatus 100 in a first testing mode, shear testing mode 170. FIG. 3 shows testing apparatus 100 re-configured into a second testing mode, tensile testing mode 180. To switch from the first testing mode to the second testing mode, the user may first detach force transfer arm 150 from second surface 130. The user may then unscrew nut 260 from force transfer arm 150 to uncouple force transfer arm 150 and force generator 160 from test frame 140. Force transfer arm 150 may then be drawn through first opening 195 so that both force transfer arm 150 and force generator 160 may be detached from test frame 140. Force generator 160 may then be aligned with second opening 205 on cover 200, for example by centering spring 240 around second opening 205. Force transfer arm 150 may then be passed through spring 240 and second opening 205 to extend through test frame 140 and to second surface 130. Nut 260 may then be threaded onto force transfer arm 150 until the desired amount of compression of spring 240 is achieved. Force transfer arm 150 may then be attached to second surface 130 so that testing apparatus is now in the second mode, the tensile testing mode as shown in FIG. 3.

Figure 8:
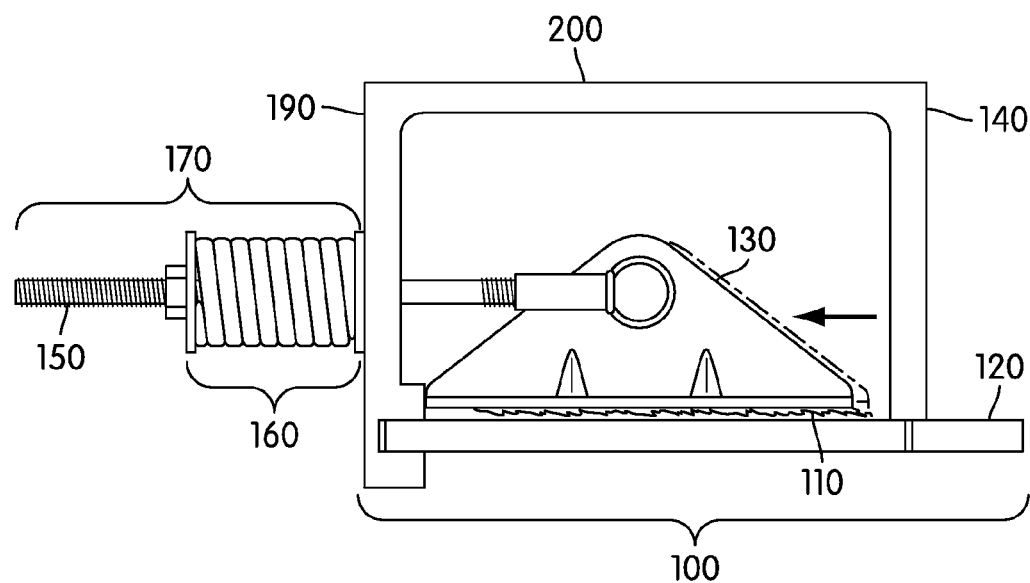
FIG. 8 is a side view of the testing apparatus shown in FIG. 2 after the system has been tested to failure.

In use, testing apparatus 100 applies a load to adhesive layer 110, such as to note the durability of adhesive layer 110 or until adhesive layer fails. As shown in FIG. 2, testing apparatus 100 is configured in shear testing mode 170. In shear testing mode 170, force generator 160 is disposed against an outside surface of first wall 190. In this embodiment, first wall 190 is substantially orthogonal to first surface 120 and adhesive layer 110. Force generator 160 and force transfer arm 150 are also positioned substantially orthogonally to first wall 190 and, therefore, substantially parallel to first surface 120 and adhesive layer 110. Thus, when force generator 160 produces a force, force transfer arm 150 attempts to drag second surface 130 toward first wall 190. This produces a shearing load in adhesive layer 110. FIG. 8 shows how adhesive layer 110 fails when subjected to a shearing load. Second surface 130 slides or slips along second surface 120 in the direction of the arrow. Adhesive layer 110 fails to allow for the movement of second surface 130 to its failure position.

Figure 9:
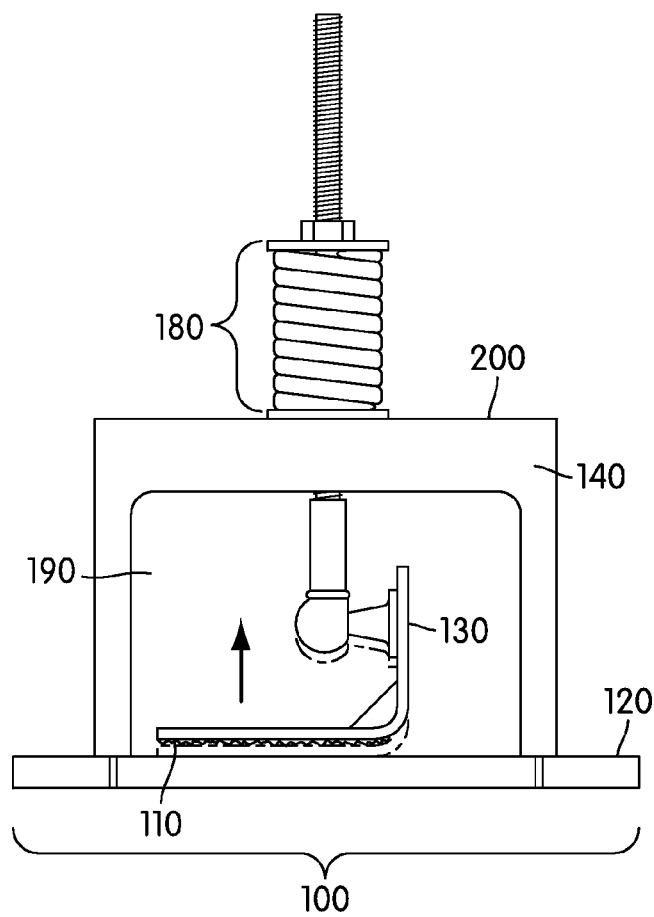
FIG. 9 is a side view of the testing apparatus shown in FIG. 3 after the system has been tested to failure.
Figure 10:
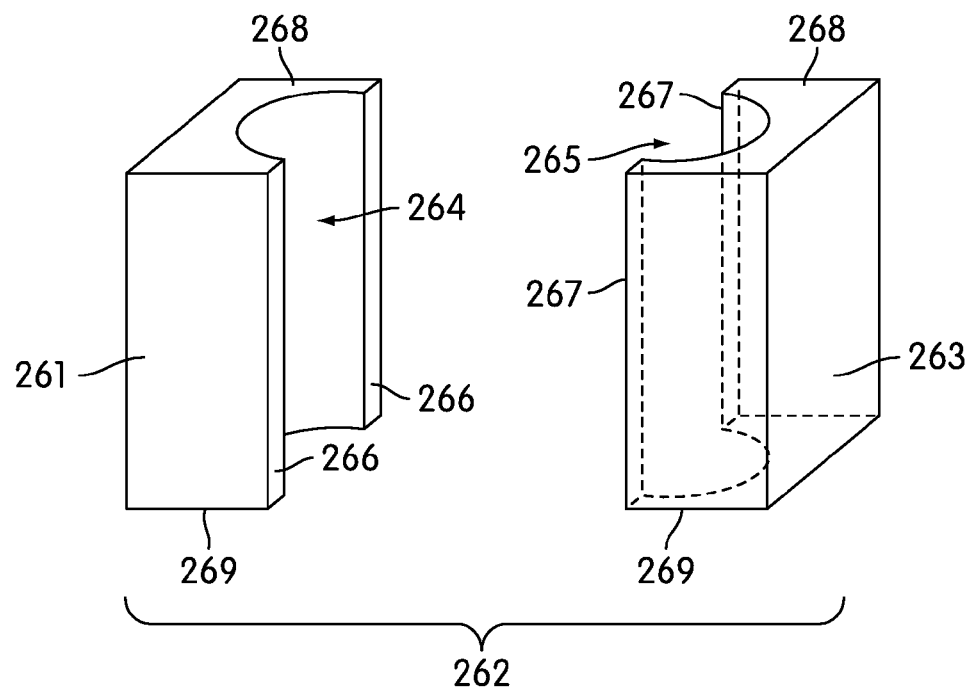
FIG. 10 is a perspective view of an embodiment of a spacer in an open position.
Figure 11:
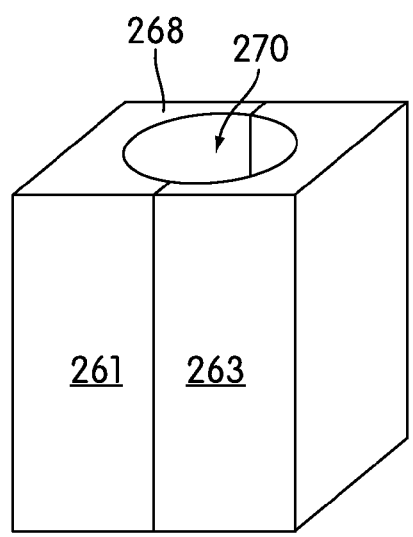
FIG. 11 is a perspective view of the spacer of FIG. 10 is a closed position.
Figure 12:
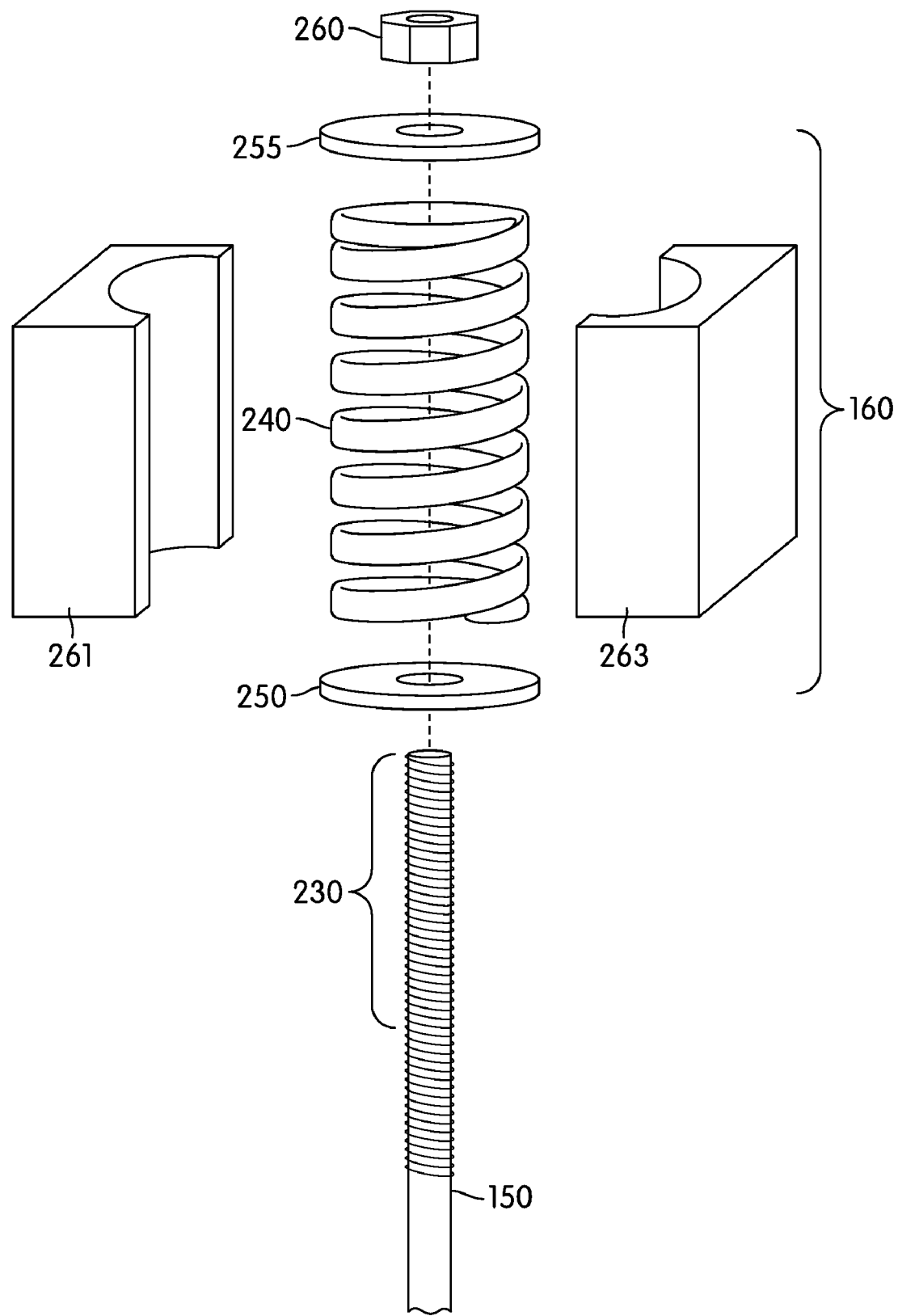
FIG. 12 is an exploded view of a portion of an embodiment of a creep tester with an embodiment of a spacer.

As shown in FIG. 3, testing apparatus 100 is configured in tensile testing mode 180. In tensile testing mode 180, force generator 160 is disposed against an outside surface of cover 200. In this embodiment, cover 200 is substantially parallel to first surface 120 and adhesive layer 110. Force generator 160 and force transfer arm 150 are positioned substantially orthogonally to cover 200 and, therefore, substantially orthogonally to first surface 120 and adhesive layer 110. Thus, when force generator 160 produces a force, force transfer arm 150 attempts to pull second surface 130 away from cover 190. This produces a tensile load in adhesive layer 110. FIG. 9 shows how adhesive layer 110 fails when subjected to a tensile load. Second surface 130 pulls away from second surface 120 in the direction of the arrow. Adhesive layer 110 fails, such as by breaking in some embodiments, to allow for the movement of second surface 130 to its failure position.

When using an attachment such as ball joint attachment 152, force transfer arm 150 may be moved from one testing mode, such as shear test mode 170, to another testing mode, such as tensile test mode 180, without removing force generator 160 from testing apparatus 100. As discussed above, ball joint attachment 152 is configured to allow force transfer arm 150 to rotate with respect to second surface 130 to move from one testing mode to another. In the embodiment shown in FIGS. 1-4, frame 140 may need to be removed from first surface 120 to enable the rotation from one testing mode to another. In another embodiment, shown in FIGS. 17-21, the testing jig may be configured to easily allow shifting from one mode of testing to another mode of testing by rotating force generator 160 from one mode to another without removing force transfer arm 150 from second surface 130 and without significantly disassembling the testing jig.

In the test apparatus 300 embodiment shown in FIGS. 17-21, frame 140 is similar to the frame described with respect to the embodiment shown in FIGS. 1-4. However, test apparatus 300 includes at least two features to enable a fast change from one testing mode to another: a transition channel 302 and a testing surface holder 308.

Transition channel 302 allows force transfer arm 150 to rotate from a first mode to another testing mode without moving frame 140. Transition channel is an opening formed in the walls of frame 140 against which force generator 160 presses to create the shear and tensile forces to be transferred to second surface 130. For example, in the embodiment shown in the figures, a first portion 306 of transition channel 302 is formed in first wall 390, the wall against which force generator 160 presses in shear test mode 170. First portion 306 terminates at first rest 395. First rest 395 may be sized and shaped to allow force transfer arm 150 to rest securely at first rest 395. For example, if force transfer arm 150 is a cylindrical rod, first rest 395 may be a curved surface. In another embodiment, where force transfer arm 150 may be a rod having a square or rectangular cross-section, first rest 395 may be a flat surface. First rest 395 may be positioned on first wall 390 so that force transfer arm 150 can be readily positioned orthogonally to first wall 390, as shown in FIG. 19.

A second portion 304 of transition channel 302 is formed in cover 200, the wall against which force generator 160 presses in tensile test mode 180. Second portion 306 terminates at second rest 305. Second rest 305 may be sized and shaped to allow force transfer arm 150 to rest securely at second rest 305. Second rest 305 may be positioned on cover 200 so that force transfer arm 150 can be readily positioned orthogonally to cover 200, as shown in FIG. 21.

Test apparatus 300 also includes testing surface holder 308. Testing surface holder 308 traps a portion of first surface 120 between two portions: an upper portion 312 and a lower portion 314. Upper portion 312 and lower portion 314 are spaced apart from each other to form a gap 316. Gap 316 is sized and shaped to receive a portion of first surface 120. When held within gap 316, first surface 120 is stabilized so that a single testing jig can be used to apply a shear force and a tensile force. Without gap 316, first surface 120 may become unstable over the duration of a test, particularly when a shear force is applied. This instability may result in rotational forces being introduced to the testing surfaces. Testing surface holder 308 helps to eliminate these rotational forces. As will be recognized by those in the art, testing holder 308 may be used in any embodiment.

Figure 19:
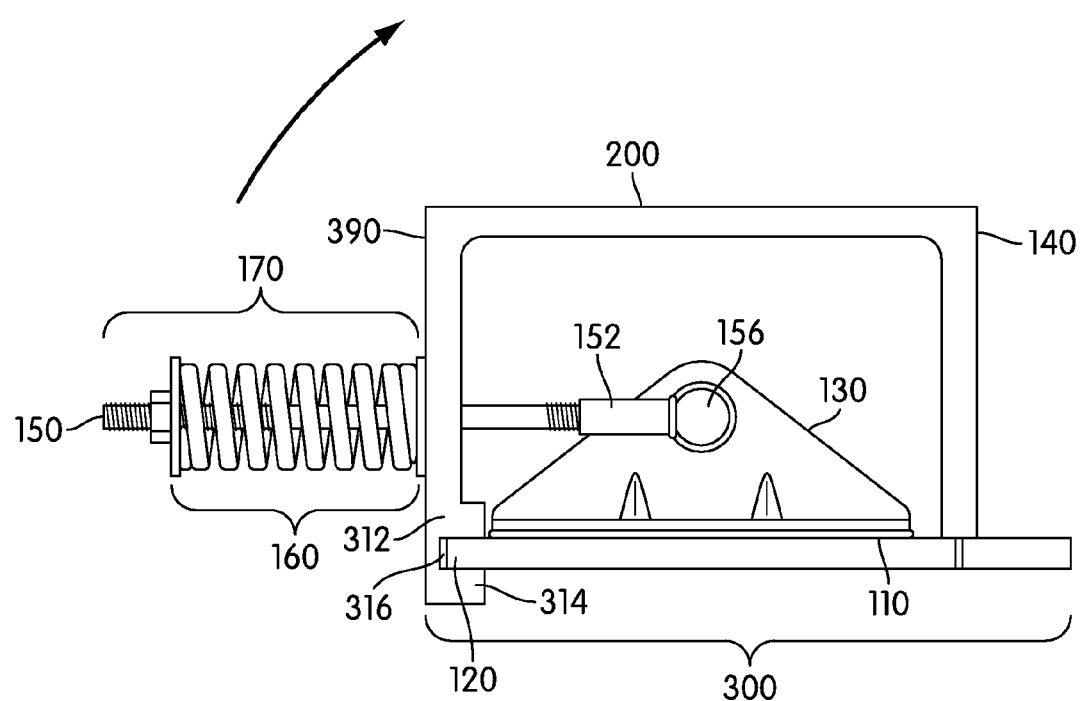
FIG. 19 is a side view of a testing apparatus in a first testing position.
Figure 20:
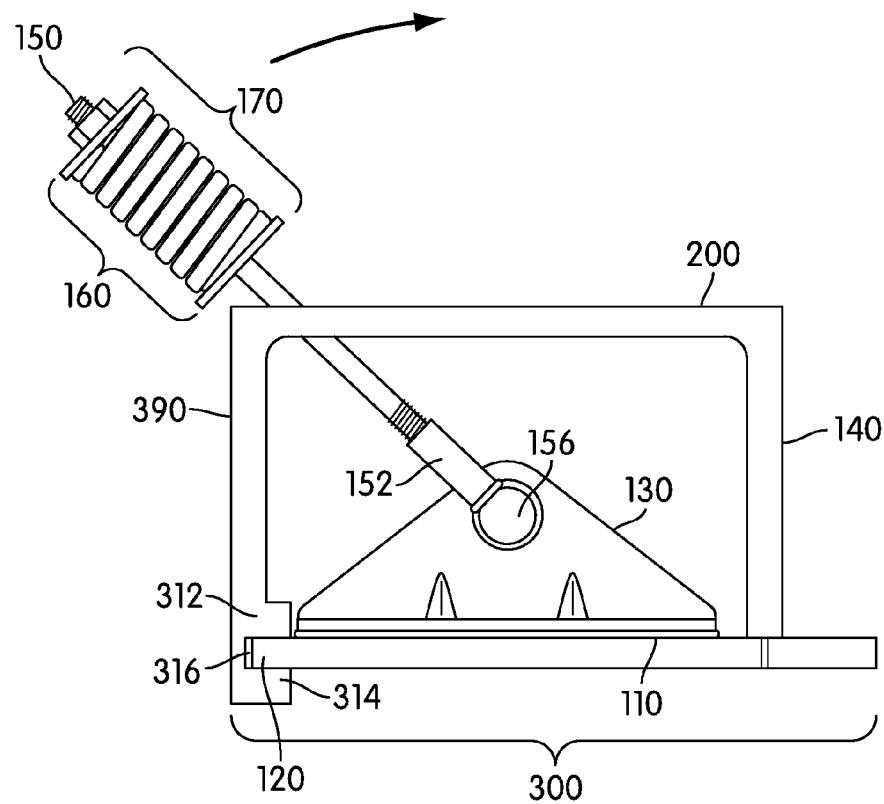
FIG. 20 is a side view of the testing apparatus of FIG. 19 in an intermediate position as the force transfer mechanism moves from the first testing position to a second testing position.
Figure 21:
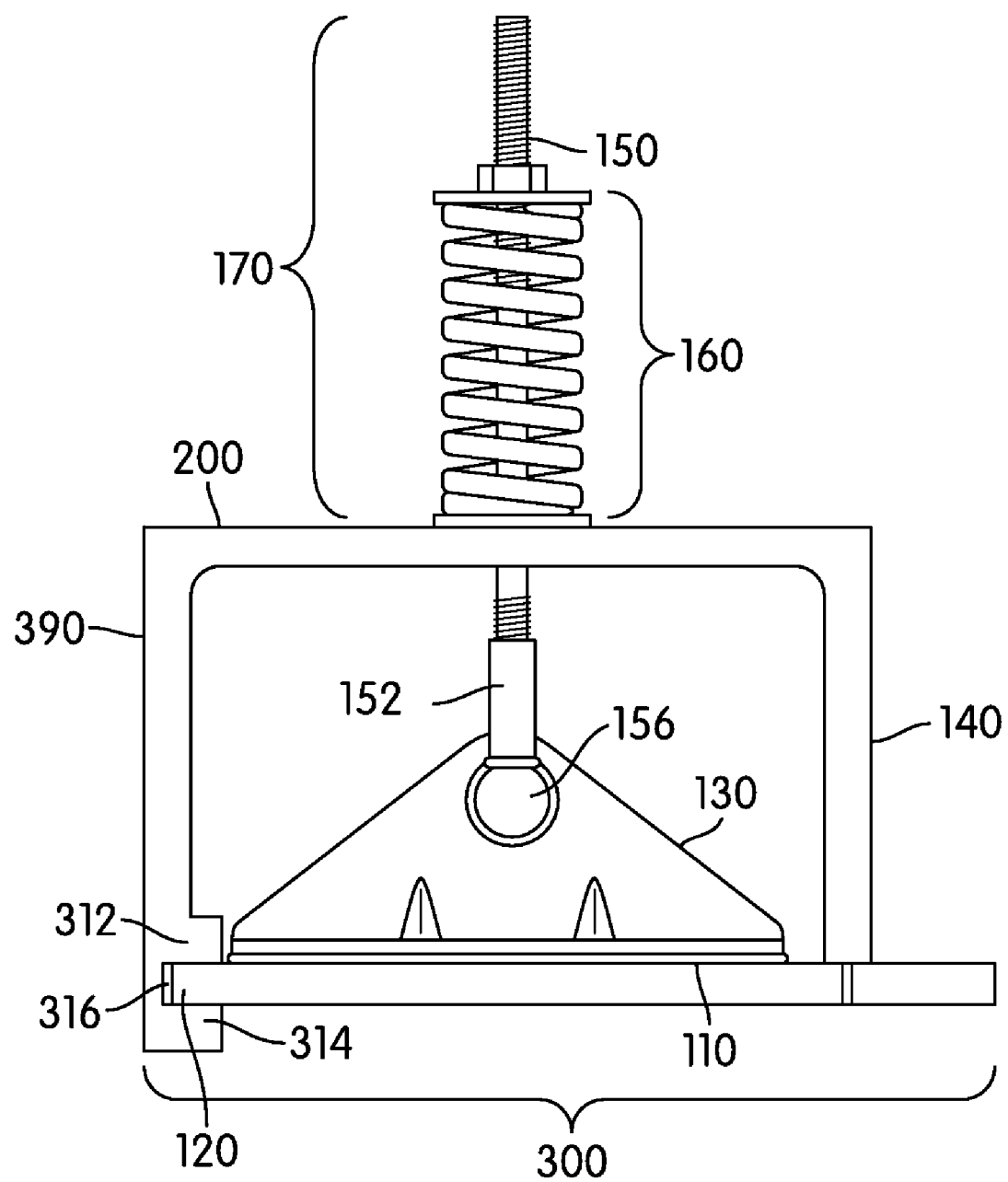
FIG. 21 is a side view of the testing apparatus of FIGS. 19 and 20 in the second testing position.

FIGS. 19-21 show one embodiment of how force generator 160 may be moved from a first test mode to a second test mode. For the purposes of this example, test apparatus 300 is starting in shear test mode 170 and transitions to tensile test mode 180. FIG. 19 shows test apparatus in shear test mode 170. Force transfer arm 150 extends orthogonally away from first wall 390, and force generator 160 abuts first wall 390.

To change from shear test mode 170 to tensile test mode 180, force transfer arm 150 is moved to extend orthogonally away from cover 200, as shown in FIG. 21. As shown in FIG. 20, force generator 160 is moved away from first wall 390 so that force generator 160 can clear the walls of test apparatus 300. This can be done manually, such as using fingers or a tool to loosen a nut holding the spring of force generator 160 in position. The spring may then slide along force transfer arm 150 away from first wall 390 until the desired length is provided between force generator 160 and first wall 390. In some embodiments, the spring may be compressed as shown in FIG. 20 to assist in clearing the walls of test apparatus, for example, when force transfer arm 150 is relatively short.

Force transfer arm 150 is then rotated on ball joint attachment 152 with a pivot point of head 560 of ball joint attachment 152, as shown in FIG. 20. FIG. 20 shows an intermediate position of force transfer arm 150, approximately halfway between the shear mode position and the tensile mode position.

Force transfer arm 150 is rotated until force transfer arm 150 is in the desired position. As shown in FIG. 21, force transfer arm 150 may be rotated until force transfer arm 150 is positioned orthogonal to cover 200 for tensile test mode 180. Force generator 160 is moved again to abut cover 200 so that a testing force can be applied. This can be accomplished, for example, by threading the nut of force generator 160 along force transfer arm 150. Because the shear mode may have been tested to complete failure of the adhesive layer, an additional layer of adhesive may be applied to reaffix second surface 130 to first surface 120.

Figure 22:
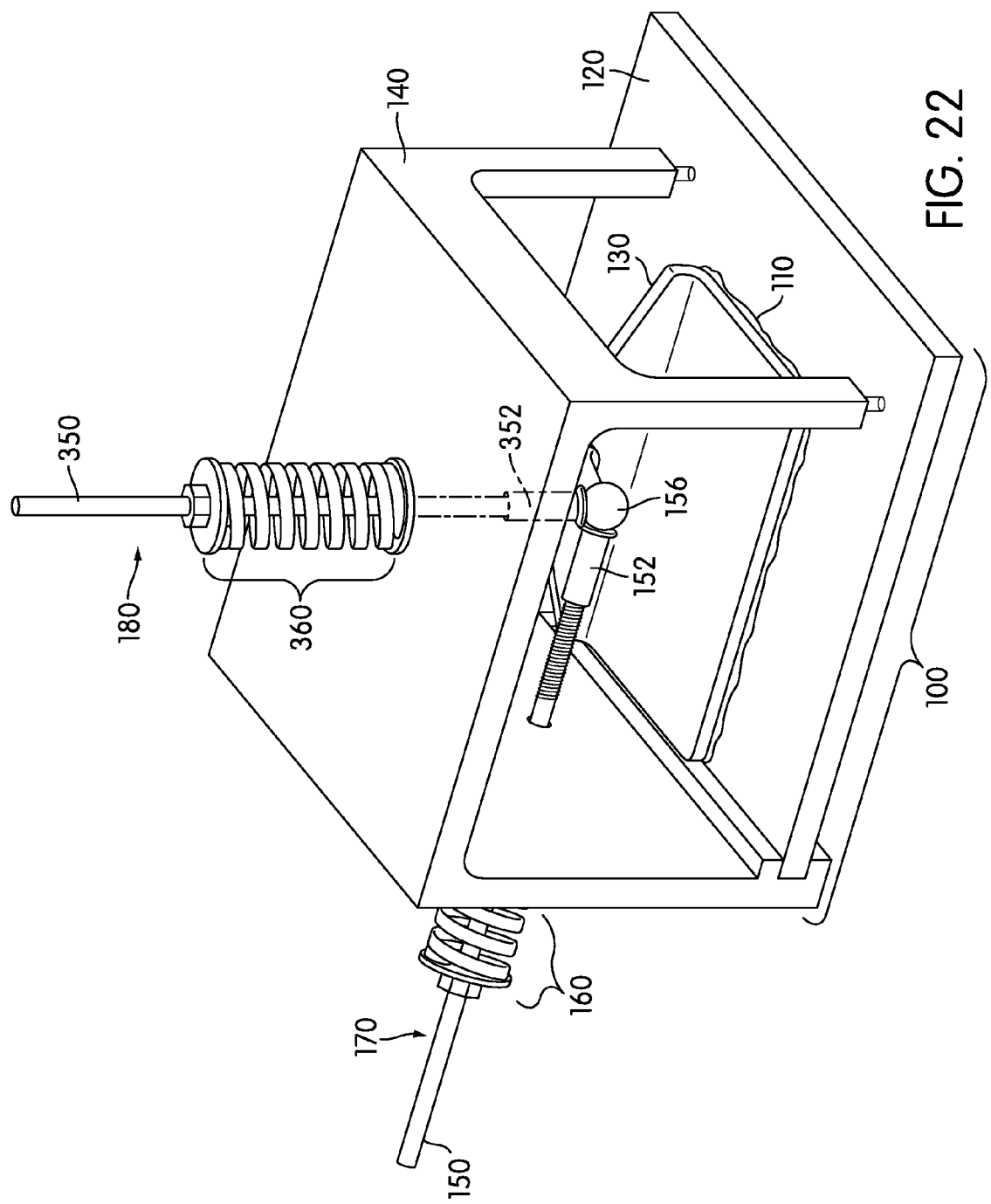
FIG. 22 is a perspective view of a testing apparatus capable of testing an adhesive simultaneously in two modes.

In some embodiments, simultaneous testing in multiple modes may be performed. As shown in FIG. 22, this may be accomplished by having two force transfer arms, a first force transfer arm 150 and a second force transfer arm 350 associated with a single ball joint head 156. First force transfer arm 150 includes a first force generator 160, and second force transfer arm 350 includes a second force generator 360. First force transfer arm 150 is attached to ball joint head 156 by first ball joint attachment 152, and second force transfer arm 350 is attached to ball joint head 156 by second ball joint attachment 352. First ball joint attachment 152 and second ball point attachment 352 may be associated with ball joint head 156 using any method known in the art, such as by welding or co-forming.

First force transfer arm 150 and second force transfer arm 350 may be positioned orthogonally or substantially orthogonally to each other, as shown in FIG. 22. In the embodiment shown in FIG. 22, first force transfer arm 150 is associated with the test apparatus in shear test mode 170, and second force transfer arm 350 is associated with the test apparatus in tensile test mode 180. This configuration allows for both testing modes to be performed at the same time, allowing the tester to simulate various real-world situations with both shear and tensile forces applied simultaneously.

While various embodiments of the invention have been described, the description is intended to be exemplary, rather than limiting and it will be apparent to those of ordinary skill in the art that many more embodiments and implementations are possible that are within the scope of the invention. Accordingly, the invention is not to be restricted except in light of the attached claims and their equivalents. Also, various modifications and changes may be made within the scope of the attached claims.

I claim:

1. A testing apparatus comprising:
   a first testing surface;
   a second testing surface adhered to the first testing surface with a layer of an adhesive;
   a first wall associated with the first testing surface;
   a second wall attached to the first wall, wherein the second wall is positioned orthogonally to the first wall;
   a force generator associated with the second testing surface, wherein the force generator can generate a constant force;
   a force transfer arm associated with the force generator, wherein the force transfer arm transfers the constant force from the force generator to the second surface;
   the force transfer arm associated with the second testing surface with a ball joint so that the force generator is rotatably attached to the second testing surface;
   wherein the testing apparatus tests the adhesive capability of the adhesive in a first mode when the force transfer arm extends through the first wall so that the force generator is positioned against the first wall;
   wherein the testing apparatus tests the adhesive capability of the adhesive in a second mode when the force transfer arm extends through the second wall so that the force generator is positioned against the first wall;
   and wherein the force transfer arm is rotated on the ball joint to move from the first mode to the second mode.

2. The testing apparatus of claim 1, wherein the first mode is shear loading and the second mode is tensile loading.

3. The testing apparatus of claim 1, wherein the first surface comprises a glass plate and the second surface comprises a component for use in a commercial device.

4. The testing apparatus of claim 1, wherein the first wall includes a surface holder comprising a gap defined by an upper portion and a lower portion, wherein the first surface is associated with the first wall by inserting the first surface into the gap.

5. The testing apparatus of claim 1 further comprising a transfer channel formed in the first wall and the second wall, wherein the transfer channel accommodates the rotation of the force transfer arm from the first mode to the second mode.

6. An adhesive tester comprising:
   a frame;
   a force generator attached to the frame for generating a test force;
   a force transfer arm configured to transfer the test force from the force generator to an adhesive layer disposed between a glass surface and a second surface;
   a ball joint attaching the force transfer arm to the second surface;
   wherein the force generator may be attached to the frame in any one of a plurality of orientations; and
   wherein the ball joint isolates rotational forces from being transferred from the force transfer arm to the second surface.

7. The adhesive tester of claim 6, wherein the test force comprises a tensile force.

8. The adhesive tester of claim 6, wherein the test force comprises a shear force.

9. The adhesive tester of claim 6, wherein the force generator comprises a constant load generator.

10. The adhesive tester of claim 9, wherein the force generator comprises a spring.

11. The adhesive tester of claim 9 further comprising a spacer configured to limit the spring.

12. The adhesive tester of claim 6, wherein the frame is configured to be disposed on one of the glass surface or the second surface.

13. The adhesive tester of claim 12, wherein the frame receives a portion of the other of the glass surface or the second surface in a gap associated with a wall of the frame.

14. The adhesive tester of claim 6, wherein the frame comprises a cage having a first wall and a second wall disposed orthogonally to the first wall.

15. The adhesive tester of claim 14, wherein the force transfer arm is configured to extend through either the first wall or the second wall.

16. The adhesive tester of claim 6 further comprising a second force transfer arm, wherein the force transfer arm and the second force transfer arm are both attached to the ball joint.

17. The adhesive tester of claim 6, wherein the second surface comprises a component for use in a commercial product.

18. A method of testing an adhesive, the method comprising the steps of:

positioning a force generator on a test frame in a first mode configuration;

removably attaching a first test surface to the force generator with a force transfer arm, wherein the first test surface is adhered to a glass surface with a first layer of an adhesive, and wherein the force transfer arm is attached to the first test surface with a ball joint;

applying a first load until the first layer of the adhesive fails;

rotating the force transfer arm on the ball joint to position the generator on the test frame in a second mode configuration;

adhering the first test surface to the glass surface with a second layer of the adhesive; and applying a second load until the second layer of the adhesive fails.

19. The method of claim 18, wherein repositioning the force generator on the test frame comprises moving the force transfer arm through a channel formed in the test frame.

20. The method of claim 18, further comprising the step of placing the test frame, the glass surface, and the first test surface into an environmental chamber prior to applying the first load.

* * * * *